US008435929B2

(12) United States Patent
Silverman et al.

(10) Patent No.: US 8,435,929 B2
(45) Date of Patent: May 7, 2013

(54) 1-AMINOCYCLOPROPANE CARBOXYLIC ACID AS A FRUIT THINNER

(75) Inventors: Franklin Paul Silverman, Highland Park, IL (US); Jim Hansen, Bensenville, IL (US); Gregory D. Venburg, Deerfield, IL (US); Derek D. Woolard, Zion, IL (US); Gregory G. Clarke, Dillsburg, PA (US); Michael Schroeder, Guggenhausen (DE); Andrew Rath, Underwood (AU); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 132 days.

(21) Appl. No.: 12/813,640

(22) Filed: Jun. 11, 2010

(65) Prior Publication Data
US 2010/0317529 A1  Dec. 16, 2010

Related U.S. Application Data

(60) Provisional application No. 61/186,413, filed on Jun. 12, 2009.

(51) Int. Cl.
*A01N 37/00* (2006.01)
(52) U.S. Cl.
USPC .......................................... 504/307; 504/320
(58) Field of Classification Search .................. None
See application file for complete search history.

(56) References Cited

U.S. PATENT DOCUMENTS
2009/0011939 A1 * 1/2009 Thrower et al. ............... 504/319

OTHER PUBLICATIONS

Tittle(Auxin-stimulated ethylene production in fern gametophytes and sporophytes, Physiloogia Plantarum, 1987, 70 No. 3, 499-502).*
Hayama et al.(Regulation of stony hard peach softening with ACC treatment, Postharvest Biology and Technology, 2008, 50 No. 2-3, 231-2).*
Brecht et al.(J. of American Society of Horticultural Science, 1984, 109, No. 6, 869-72).*
Miller et al.(J. of American Society of Horticultural Science, 1988, 113, No. 1, 119-24).*
Byers et al., "Flower and Fruit Thinning of Peach and Other Prunus", Horticulture Reviews, vol. 28, 2003, pp. 351-392.
Cawthorn et al., "Preliminary Observations on use of Ethylene-Releasing Compounds for Chemical Peach Thinning in North Texas", Texas Agricultural Experiment Station, PR-4206 Jul. 1984, pp. 1-4.
Costa et al., "Fruit thinning of peach trees", Plant Growth Regulation 31: 2000, pp. 113-119.
F.G. Dennis. Jr., "The history of fruit thinning", Plant Growth Regulation 31: 2000. pp. 1-16.
Olien et al., "Interaction between temperature and ethylene in sour cherry fruit abscission[1]", HortScience 17(5): 1982, pp. 795-796.
Olien et al., "The effect of ethephon-induced gum accumulation in sour cherry (prunes *cerasus* I..) on shoot water relations and hydraulic conductance", Acta Horticulturae 137, 1983, pp. 55-64.
Petracek et al., "A history of commercial plant growth regulators in apple production", HortScience, vol. 38(5), Aug. 2003, pp. 937-942.
Yuan et al., "Benzyoladenine as a chemical thinner for 'McIntosh' applies. 1. fruit thinning effectls and associated relationships with photosynthesis, assimilate translocation, and nonstructural carbohydrates", J. Amer. Soc. Hort. Sci. 125(2), 2000, pp. 169-176.
Gambrell et al., "Results of eight years with CGA-15281 as a postbloom thinner for peaches", J. Amer. Soc. Hort. Sci. 108(4) 1983; pp. 605-608.
Byers, "Chemical thinning of peach fruits with CGA 15281 and CGA 17859[1]", J. Amer. Soc. Hort. Set. 103(2) 1978, pp. 232-236.
Olien et al., "The effect of temperature on rate of ethylene evolution from ethephon and from ethephon-treated leaves of sour cherry[1]", J. Amer. Soc. Hort. Sci. 103(2) 1978, pp. 199-202.
Olien et al., "Ethylene generation temperature responses, and relative biological activities of several compounds with potential for promoting abscission of sour cherry fruit[1]", J. Amer. Soc. Hort. Sci. 107(6) 1982. pp. 1085-1089.
Weinbaum et al., "Chemical thinning: ethylene and pre-treatment fruit size influence enlargement, auxin transport and apparent sink strength of French prune and 'andross' peach[1]", J. Amer. Soc. Hort. Sci. 102(6) 1977, pp. 781-785.
Wittenbach et al., "Cherry fruit abscission: effect of growth substances, metabolic inhibitors and environmental factors[1]", J. Amer. Soc. Hort. Sci. 98(4) 1973, pp. 348-351.

* cited by examiner

*Primary Examiner* — Alton Pryor
(74) *Attorney, Agent, or Firm* — Wood, Phillips, Katz, Clark & Mortimer

(57) ABSTRACT

The present invention relates to agricultural methods and compositions of 1-aminocyclopropane carboxylic acid (ACC) alone or in combination with 2-chloroethylphosphonic acid (ethephon) to reduce crop load of fruit trees.

5 Claims, No Drawings

1-AMINOCYCLOPROPANE CARBOXYLIC ACID AS A FRUIT THINNER

FIELD OF THE INVENTION

The present invention relates to agricultural methods and compositions of 1-aminocyclopropane carboxylic acid (ACC) alone or in combination with 2-chloroethylphosphonic acid (ethephon) to reduce crop load of fruit trees.

BACKGROUND OF THE INVENTION

Stone fruits such as almond, apricot, cherry, nectarine, peach, and plum are important perennial fruit crops in the US and around the world. There is an increasing emphasis on producing larger fruit of high quality, as opposed to volume of fruit (tonnage). Growers are now challenged to produce crops of uniformly large fruit with adequate color and optimal flavor as consumers have grown to expect high quality fruit on a year round basis.

Reduction of the crop load on a tree (thinning) is often used to produce high quality tree fruit. During flowering and fruit set, growers commonly physically or chemically remove flowers (flower thinning) or young fruit (fruitlet thinning) to maximize the size and quality of the remaining fruit (Dennis, 2000, Plant Growth Reg. 31: 1-16). In general, the earlier the crop load is 'thinned' the better the quality of fruit at harvest. Removal of flowers or fruitlets on each tree by hand (hand thinning) often provides consistent results but can be prohibitively expensive. The use of chemicals for cost-effective flower or fruitlet thinning is preferable. The chemical insecticide carbaryl is often used for thinning apple fruitlets (Petracek et al., 2003, HortScience. 38: 937-942). However, carbaryl faces regulatory challenges and is no longer available to growers in some regions. The cytokinin 6-benzyladenine (6BA) is an important thinning chemical and is particularly effective for increasing fruit size. However, 6BA-induced thinning is sensitive to physiological and weather conditions (Yuan and Greene, 2000, J. Amer. Soc. Hort. Sci. 125: 169-176). For stone fruit such as peaches, there are currently no chemicals that safely and consistently induce post-bloom thinning (Costa and Vizzotto, 2000, Plant Growth Reg. 31: 113-119; Byers et al., 2003, In: Janick ed. Horticultural Reviews, John Wiley and Sons, Inc., 351-391). As Byers stated in 1978 (J. Amer. Soc. Hort. Sci. 103:232-236) "The search for an effective chemical peach thinning agent has not resulted in a commercially acceptable method of fruit removal. Numerous materials have been tried and most have been discarded due to inconsistent results, leaf abscission, fruit deformation, or unacceptable timing in relation to bloom and the frost period." After more than 30 years since this publication, there is still a need for new chemicals that safely and consistently reduce crop load in these and other tree fruit crops.

Ethylene and ethylene-releasing compounds have been tested for apple, pear, and stone fruit thinning. Ethephon is a commercially available ethylene-releasing agent that has been extensively evaluated as a stone fruit thinner. Unfortunately, ethephon produces unreliable thinning results in part because ethylene release from ethephon degradation is inconsistent. Among factors, temperature greatly affects ethylene release rates (Wittenbach and Bukovac 1973, J. Amer. Soc. Hort. Sci. 98: 348-351; Olien and Bukovac, 1978, J. Amer. Soc. Hort. Sci. 103: 199-202; Olien and Bukovac 1982 HortScience 17: 795-796). For example, ethylene evolution from ethephon-treated sweet cherry shoots increased 4- to 6-fold when temperature increased from 20 to 30 C (Olien and Bukovac, 1978, J. Amer. Soc. Hort. Sci. 103: 199-202). Since temperatures change rapidly during the thinning season, predicting the appropriate ethephon dose is difficult and often results in under- or over-thinning (Olien, W. C. and M. J. Bukovac, 1978, J. Amer. Soc. Hort. Sci. 103: 199-202; Olien, W. C. and M. J. Bukovac, 1982, J. Amer. Soc. Hort. Sci. 107: 1085-1089; Cawthon et al. 1984, Texas PR 4206. Texas Agric. Expr. Stn., Overton, Tex.).

In addition to an unpredictable thinning response, ethephon may cause significant defoliation, even when thinning is only moderate (Gambrell et al. 1983. J. Amer. Soc. Hort. Sci. 108: 605-608). Ethephon also has been shown to reduce final fruit size (Weinbaum et al., 1977. J. Amer. Soc. Hort. Sci. 102: 781-785) which negates one of the major desired quality outcomes of thinning. Moreover, ethephon application has been implicated in causing a physiological disorder called gummosis (Olien and Bukovac, 1983, Acta Hort. 137: 55-64). Gummosis is a generalized disorder of trees in which polysaccharide gum is overproduced, exuded, and deposited on the bark. Gummosis affects water relations, promotes disease, is attractive to wood-boring insects, causes shoot death, and leads to early tree decline.

Thus, although ethephon has provided some positive results, it is not currently registered for this use because of inconsistent thinning due to environmental and physiological factors, extensive leaf drop, and stimulation of gummosis (Costa and Vizzotto, 2000. Plant Growth Reg. 31: 113-119; Byers et al., 2003, Horticultural Reviews, J. Janick, ed. John Wiley and Sons, Inc. p. 351-391; Olien and Bukovac, 1983, Acta Hort. 137: 55-64). Consequently the external application of ethylene to trees (e.g. through the use of products like ethephon which are sprayed onto trees) is not recommended as a thinning agent for stone fruit.

It is an object of this invention to reduce the crop load of stone fruits, such as peaches, using ACC during the growing season.

It is an object of this invention to reduce the crop load of pome fruits, such as apples, using ACC alone or in combination with other thinners, applying it during the growing season.

It is a further object of the present invention to use ACC to increase the quality of stone fruit.

It is a further object of the present invention to use ACC and ethephon combinations to increase the quality of stone fruit.

It is an object of this invention to show the unexpected finding that induction of the plants ethylene production by ACC is inhibited at 35° C. or higher temperatures.

It is an object of this invention to demonstrate that ethephon and ACC have differential ethylene release profiles and differential physiological effects in response to temperature.

SUMMARY OF THE INVENTION

The present invention is directed to a method of thinning stone fruit by applying ACC as a foliar spray at bloom or following bloom.

The present invention is also directed to a method of thinning stone fruit by applying ACC alone or in combination with ethephon as a foliar spray during bloom.

The present invention is also directed to a method of thinning stone fruit by applying ACC in combination with ethylene generators as a foliar spray during bloom.

The present invention is further directed to an agricultural composition that comprises ACC and effective adjuvants.

The present invention is further directed to an agricultural composition that comprises ACC and ethephon.

DETAILED DESCRIPTION OF THE INVENTION

The present invention comprises the application of ACC alone or in combination with other active ingredients. The composition of the present invention may contain from 0.01 to 50 wt % ACC. Other active ingredients may be used in combination with ACC include, but not limited to, plant growth regulators such as gibberellins, cytokinins, auxins, abscisic acid, or plant growth regulator antagonists, fungicides, bactericides, nematicides, insecticides, or herbicides.

The present invention comprises the application of ACC with adjuvants such as surfactants, oils, soaps, and salts.

The present invention can be used to reduce cropload of stone fruit. ACC, ACC salt, or ACC formulation is applied to the trees as a foliar spray during bloom or at fruitlet stage. This application results in substantial reductions in crop load (thinning).

For these all studies, the chemicals used were purchased commercially. 1-Aminocyclopropane carboxylic acid (ACC) was purchased from Sigma-Aldrich (Saint Louis, Mo. USA) or Senn Chemicals (San Diego, Calif., USA). 2-Chloroethylphosphonic acid (ethephon) was purchased from Southern Agricultural Insecticides Inc. (Hendersonville, N.C., USA) as the product Florel®, a 3.9% (w/w) solution. The spray adjuvant L-77 was obtained from OSI Specialties (Greenwich, Conn., USA).

For thinning studies, peach and apple trees and grape vines were selected for uniformity. For peach and apple studies, individual branches were flagged for each treatment on each replicate tree so that each replicate tree had one flagged branch for each treatment. The number of fruit on each tagged limb was recorded to serve as a pre-treatment count for determination of the percentage of fruit retention following treatment. The flagged branches were sprayed to runoff with treatment solution and care was taken to shield the remainder of the tree from spray drift. The number of fruit remaining on the tagged limbs was counted within a month after treatment and the percentage of fruit remaining (fruit set) was determined. For grape studies, clusters were flagged and sprayed to runoff with treatment solution. At harvest, cluster weight, berry weight, berry number and rachis length were measured and number of berries per rachis was calculated.

For laboratory and growth chamber studies, deionized ultra-pure water was used in preparing solutions. Spray solutions were used as soon as possible after mixing. All spray solutions were amended with spray adjuvants as appropriate. A cotton cotyledon bioassay was used in the laboratory to study the effects of ACC or ethephon on induction of ethylene. Ten day old cotton plants with fully expanded cotyledons were used. Sprays were made to the upper (adaxial) surface of the leaves and the plants were then incubated in growth cabinets at the temperatures indicated. The cotyledons were excised at the times indicated and placed in sealed plastic vials. Headspace ethylene samples were measured on a Hewlett Packard 5890 gas chromatograph equipped with a packed Haysep T column (Alltech, Deerfield, Ill.) and a flame ionization detector.

Example 1

ACC Thinning of Stone Fruit:

A series of field studies on stone fruit thinning were performed over several seasons, on different varieties and in various locations to determine the consistency of the thinning effect of ACC. Even without the application of a chemical thinning agent, crop load (number of fruit remaining divided by the number of flowers or fruit prior to application) was variable. Chemical thinning of stone fruit is variable and dependent on many factors including variety and environment. An acceptable chemical thinning agent is one that gives a substantial and relatively consistent reduction in crop load for a given dose over a wide range of trials.

The effect of ACC rate and timing was determined. ACC was sprayed on Babygold #5 peach trees at bloom (Table 1) or shuck split (early fruitlet stage) (Table 2). Application of 300 ppm ACC at bloom or shuck split resulted in a moderate crop load (57 or 61% of the flowers remained on the tree to become fruit). Application of 1000 ppm ACC at bloom or shuck split resulted in a lower fruit set (30 or 11%). Application of 300 ppm of ACC at bloom resulted in a reduced cropload of 77% whereas 1000 ppm of ACC resulted in a greater reduction of the cropload to only 40%.

TABLE 1

Effect of ACC application at bloom on fruit set of Babygold #5 peach

| Treatment | Percent fruit set | Crop load (percent) of treated trees compared to the water control |
|---|---|---|
| Water control | 75 | 100 |
| 100 ppm ACC | 67 | 90 |
| 300 ppm ACC | 57 | 77 |
| 1000 ppm ACC | 30 | 40 |

TABLE 2

Effect of ACC application at shuck split on fruit set of Babygold #5 peach. All treatments had 0.05% Regulaid adjuvant included.

| Treatment | Percent fruit set | Crop load (percent) of treated trees compared to the water control |
|---|---|---|
| Water control | 84 | 100 |
| 100 ppm ACC | 85 | 102 |
| 300 ppm ACC | 61 | 72 |
| 1000 ppm ACC | 11 | 14 |

ACC was sprayed on Tatura 204 peach trees at late shuck fall (Table 3). Application of 300 ppm ACC resulted in a moderate fruit set (43%) and 1000 ppm ACC resulted in low fruit set (27%).

TABLE 3

Effect of ACC application at late shuck fall on fruit set of Tatura 204 peaches.

| Treatment | Percent fruit set | Crop load (percent) of treated trees compared to the untreated control |
|---|---|---|
| Control | 76 | 100 |
| 100 ppm ACC | 65 | 86 |
| 300 ppm ACC | 43 | 57 |
| 500 ppm ACC | 30 | 39 |
| 1000 ppm ACC | 27 | 36 |

These results (Tables 4, 5, and 6) show that peach thinning is dependent on. ACC dose. This application may be particularly useful if bloom is heavy. The results also show that early (bloom) and later (shuck fall) applications are both effective.

Follow up studies confirmed that higher rates (500 or 750 ppm ACC) produced a moderate to heavy crop load on Babygold #5 at two locations (Tables 8 and 9) and Garnet Beauty (Table 10).

TABLE 4

Effect of ACC application at petal fall on fruit set of Babygold #5 peaches

| Treatment | Percent fruit set | Crop load (percent) of treated trees compared to the untreated control |
|---|---|---|
| Untreated control | 48 | 100 |
| 500 ppm ACC | 32 | 67 |
| 750 ppm ACC | 24 | 50 |

TABLE 5

Effect of ACC application at petal fall on fruit set of Babygold #5 peaches.

| Treatment | Percent fruit set | Crop load (percent) of treated trees compared to the untreated control |
|---|---|---|
| Untreated control | 43 | 100 |
| 500 ppm ACC | 42 | 98 |
| 750 ppm ACC | 31 | 72 |

TABLE 6

Effect of ACC application at petal fall on fruit set of Garnet Beauty peaches.

| Treatment | Percent fruit set | Crop load (percent) of treated trees compared to the untreated control |
|---|---|---|
| Untreated control | 33 | 100 |
| 500 ppm ACC | 27 | 82 |
| 750 ppm ACC | 19 | 58 |

One benefit of thinning is that reducing fruit set increases the size of the remaining fruit. The effect of rate and timing on fruit set and fruit weight was determined on Summer Rich and O'Henry peaches (Tables 7 and 8). Application of 500 or 750 ppm ACC at petal fall or the 15 mm fruit stage produce a low fruit set and substantially increased fruit weight. Also, application of ACC at petal fall minimized leaf yellowing and leaf loss on both varieties.

TABLE 7

Effect of ACC application on fruit set, weight, or crop safety of Summer Rich peaches.

| Treatment | Percent fruit set | Crop load (percent) of treated trees compared to the untreated control | Fruit weight at maturity (g) | Crop safety on vegetation (0-4 scale) |
|---|---|---|---|---|
| Control at petal fall | 71 | 100 | 87 | 0.1 |
| 500 ppm ACC at petal fall | 39 | 55 | 140 | 0.5 |
| 750 ppm ACC at petal fall | 28 | 39 | 151 | 0.8 |
| 500 ppm ACC at 15 mm | 24 | 34 | 144 | 3.0 |
| 750 ppm ACC at 15 mm | 17 | 24 | 169 | 3.5 |

TABLE 8

Effect of ACC application on fruit set and weight of O'Henry peaches.

| Treatment | Percent fruit set | Crop load (percent) of treated trees compared to the untreated control | Fruit weight at maturity (g) | Crop safety on vegetation (0-4 scale) |
|---|---|---|---|---|
| Control at petal fall | 29 | 100 | 145 | 0.1 |
| 500 ppm ACC at petal fall | 23 | 79 | 200 | 0 |
| 750 ppm ACC at petal fall | 11 | 55 | 205 | 0.5 |
| 500 ppm ACC at 15 mm | 16 | 38 | 185 | 0.7 |
| 750 ppm ACC at 15 mm | 6 | 21 | 235 | 2.1 |

Application of ACC at late shuck fall also effectively reduced fruit set of Rose Diamond nectarines (Table 9).

TABLE 9

Effect of ACC application at late shuck fall on fruit set of Rose Diamond nectarines.

| Treatment | Percent fruit set | Crop load (percent) of treated trees compared to the untreated control |
|---|---|---|
| Control | 68 | 100 |
| 125 ppm ACC | 60 | 88 |
| 250 ppm ACC | 61 | 90 |
| 500 ppm ACC | 44 | 65 |
| 1000 ppm ACC | 16 | 24 |

Application of ACC alone at shuck split reduced fruit set in a dose dependent manner (Table 10). Application of 300 ppm ACC resulted in a moderate fruit set (58% fruit set) and 1000 ppm ACC resulted in a low fruit set (13% fruit set). Application of the combination of ACC (1000 ppm) and ABA (1000 ppm) substantially reduced fruit set (2% fruit set).

TABLE 10

Effect of ACC and ABA applications at shuck split on fruit set of PF-27 peaches.

| Treatment | Percent fruit set | Crop load (percent) of treated trees compared to the untreated control |
|---|---|---|
| Water control | 86 | 100 |
| 100 ppm ACC | 70 | 81 |
| 300 ppm ACC | 58 | 67 |
| 1000 ppm ACC | 13 | 15 |
| 1000 ppm ACC + 1000 ppm ABA | 2 | 2 |
| 1000 ppm ABA | 69 | 80 |

Example 2

Gummosis is a physiological stress response in which sap oozes from fractures in tree bark and often leads to tree decline. Use of 2-chloroethylphosphonic acid as a stone fruit thinning has been limited because it can stimulate severe incidences of gummosis of stone fruit. On Babygold #5 peaches, 2-chlorophosphonic acid reduced fruit set, but also substantially increased gummosis (Table 11). In contrast, application of ACC alone reduced fruit set reliably, but caused little gummosis. Application of ACC with ABA reduced fruit set more than ACC alone without increasing gummosis.

TABLE 11

Effect of ACC, ACC and ABA combination, or 2-chloroethylphosphonic acid applications on thinning and gummosis of Babygold #5 peaches.

| Timing | Treatment | Percent Fruit Set | Scaffold Gummosis (0 = no gummosis to 5 = severe gummosis) |
|---|---|---|---|
| 10 mm Fruitlet | Untreated Control | 48.1 | 0.5 |
| | ACC 500 ppm | 6.7 | 1.5 |
| | ACC 500 ppm + ABA 500 ppm | 4.3 | 1.2 |
| | 2-Chloroethylphosphonic acid | 8.4 | 4.7 |

Example 3

ACC Thinning of Apple:

ACC was foliar applied at the 10 or 20 mm fruit stage. Application of 300 ppm ACC at the 10 or 20 mm fruit stages moderately reduced fruit set (0.66 or 0.54 fruit/fruit cluster, respectively) compared to the control (0.83 or 0.81 fruit/fruit cluster, respectively) and substantially increased fruit weight (Table 12). Application of 100 ppm ACC was particularly effective in removing fruit when applied at the 20 mm fruit stage.

TABLE 12

Effect of ACC application at 10 or 20 mm on fruit set and fruit weight of Fuji apples.

| Treatment | Application timing | Fruit/fruit cluster | Fruit weight (g) |
|---|---|---|---|
| Control | 10 mm | 0.83 | 96 |
| 100 ppm ACC | 10 mm | 0.79 | 95 |
| 300 ppm ACC | 10 mm | 0.66 | 117 |
| 1000 ppm ACC | 10 mm | 0.28 | 157 |
| Control | 20 mm | 0.81 | 100 |
| 100 ppm ACC | 20 mm | 0.54 | 130 |
| 300 ppm ACC | 20 mm | 0.41 | 132 |
| 1000 ppm ACC | 20 mm | 0.03 | 161 |

Early applications (full bloom) of ACC on Pink Lady apples were less effective in reducing fruit number (Table 13). However, the highest rate of ACC tested (1000 ppm) reduced crop load slightly. These results suggest later stage (post-bloom) applications of ACC are most effective.

TABLE 13

Effect of ACC application at 5 days after full bloom on fruit set of Pink Lady apples.

| Treatment | Number of fruit per limb | Total number of fruit |
|---|---|---|
| 100 ppm ACC | 64 | 175 |
| 300 ppm ACC | 62 | 165 |
| 500 ppm ACC | 61 | 169 |
| 1000 ppm ACC | 58 | 124 |

Similarly, ACC applications at petal fall were not effective for thinning Fuji apples, but later applications (10 and 20 mm) were effective (Table 14).

TABLE 14

Effect of ACC application at petal fall and later timings on fruit set and fruit weight of Fuji apples.

| Treatment | Timing | Fruit per fruit cluster |
|---|---|---|
| Untreated control | | 0.46 |
| 500 ppm ACC | Petal fall | 0.49 |
| 1000 ppm ACC | Petal fall | 0.39 |
| 500 ppm ACC | 10 mm (6-7 mm) | 0.27 |
| 1000 ppm ACC | 10 mm (6-7 mm) | 0.10 |
| 500 ppm ACC | 20 mm | 0.33 |

Example 4

ACC Thinning of Grape:

Application of ACC on grapes during bloom reduced the cluster weight and number of berries/cm rachis (Table 15). However, ACC applications produce the highly undesirable effect of reducing the rachis length and cluster size. Similar results have been seen in trials on other grape varieties in Michigan, California, and Australia. These results show that ACC is not effective for all fruit crops that need thinning including grapes.

TABLE 15

Effect of ACC application at bloom on cluster weight, berry weight, berries per rachis, and rachis length of Chardonnay grapes.

| Treatment | Cluster weight (g) | Berry weight (g) | Berries per cm rachis | Rachis length (cm) |
|---|---|---|---|---|
| Control | 169 | 1.2 | 3.7 | 37 |
| 100 ppm ACC | 128 | 1.2 | 3.1 | 34 |
| 300 ppm ACC | 78 | 1.2 | 2.9 | 23 |
| 1000 ppm ACC | 24 | 1.1 | 1.6 | 14 |

Example 5

ACC Ethylene Production Profile:

Selected characteristics of ACC conversion to ethylene (i.e. dose response, time course, and temperature effect) were assessed to determine whether the relative consistency of ACC as a stone fruit and apple thinner was related to performance as an ethylene producer. In these bioassays, ACC solutions were applied to cotton cotyledons by a hand sprayer at the doses indicated and all spray solutions contained 0.05% (v/v) L-77.

In the first study, the effect of ACC dose sprays on ethylene produced by cotton cotyledons was determined. (Table 16). Cotton plants were sprayed with solution (ACC at 1, 10, 25, 50, 100, 250, 500, or 1000 ppm) and the cotyledons were excised 6 or 24 h after spraying and incubated in sealed tubes for 4 h. Ethylene levels were determined production was assayed.

TABLE 16

Effect of ACC dose sprays on ethylene produced by cotton cotyledons at 25 C.

| | Ethylene production (nl/g leaf weight/h incubated) | |
|---|---|---|
| ACC (ppm) | 6 h after spraying | 24 h after spraying |
| 0 | 2.0 | 4.8 |
| 10 | 4.2 | 13.7 |

TABLE 16-continued

Effect of ACC dose sprays on ethylene produced by cotton cotyledons at 25 C.

| | Ethylene production (nl/g leaf weight/h incubated) | |
|---|---|---|
| ACC (ppm) | 6 h after spraying | 24 h after spraying |
| 25 | 5.9 | 22.8 |
| 50 | 8.3 | 32.4 |
| 100 | 11.8 | 45.2 |
| 250 | 19.4 | 59.8 |
| 500 | 22.8 | 64.4 |
| 1000 | 25.1 | 92.1 |

These results show that ACC induces ethylene production in a consistent dose-dependent manner.

In the second study, the time course of ethylene production following application of 500 mg/liter ACC or ethephon was determined (Table 17).

TABLE 17

Time course of the effect of 500 ppm ACC or ethephon sprays on ethylene production by cotton cotyledons at 25 C.

| Time following spray application (h) | Ethylene production (nl/g leaf weight/h incubated) | |
|---|---|---|
| | ACC | Ethpho0n |
| 1 | 62.8 | 153.4 |
| 4 | 36.7 | 102.5 |
| 15 | 45.7 | 106.0 |
| 24 | 49.3 | 90.8 |
| 48 | 45.3 | 58.5 |

These results show that ACC produced a more consistent amount of ethylene release over a 48 h period than ethephon.

In the third study, the effect of temperature on ethylene production following ACC or ethephon application was determined (Table 18). The incubation of the plants following spraying and the incubation of the detached leaves were performed at 25 and 35° C.

TABLE 18

The effect of incubation temperature on ethylene production of cotton cotyledons 24 h after ACC application or ethephon sprays.

| | Ethylene production (nl/g leaf weight/h incubated) | |
|---|---|---|
| Treatment | Incubated at 25 C. | Incubated at 35 C. |
| Control | 3.8 | 1.5 |
| ACC (200 ppm) | 35.7 | 19.9 |
| Ethephon (200 ppm) | 41.0 | 133.1 |

These results show that ACC and ethephon produced an equivalent amount of ethylene at 25 C, while the synthesis of ethylene by ACC was reduced somewhat at 35 C, ethylene production from ethephon dramatically increased when the temperature was increased fruit 25 C to 35 C.

The invention claimed is:

1. A method to reduce crop load by inducing ethylene production comprising applying 100 to 1000 ppm 1-aminocyclopropane carboxylic acid to stone fruit or pome fruit trees during bloom or at the fruitlet stage.

2. A method of reducing crop load of trees by inducing ethylene production comprising foliar applications of 100 to 1000 ppm 1-aminocyclopropane carboxylic acid during bloom or at the fruitlet stage.

3. The method of claim 1 wherein the stone fruit trees are peach trees.

4. The method of claim 1 wherein the stone fruit trees are nectarine trees.

5. A method to reduce crop load by inducing ethylene production comprising applying 100 to 1000 ppm 1-aminocyclopropane carboxylic acid to apple trees during bloom or at the fruitlet stage.

* * * * *